United States Patent [19]

Müller et al.

[11] 4,333,449
[45] Jun. 8, 1982

[54] WATER RESISTANT ADHESIVE STRIP

[75] Inventors: Heinz Müller; Peter Jauchen, both of Hamburg; Bodo Szonn, Kisdorf; Rolf Schulze, Hamburg, all of Fed. Rep. of Germany

[73] Assignee: Beiersdorf Aktiengesellschaft, Fed. Rep. of Germany

[21] Appl. No.: 272,596

[22] Filed: Jun. 11, 1981

[30] Foreign Application Priority Data

Jun. 16, 1980 [DE] Fed. Rep. of Germany ....... 3022605

[51] Int. Cl.³ .............................................. A61F 13/00
[52] U.S. Cl. ..................................... 128/155; 128/156
[58] Field of Search ...................... 128/155, 156, 284; 3/1

[56] References Cited

U.S. PATENT DOCUMENTS

| 3,122,142 | 2/1964 | Crowe, Jr. | 128/156 |
| 3,842,832 | 10/1974 | Wideman et al. | 128/156 |
| 4,146,027 | 3/1979 | Hoey | 128/156 |

Primary Examiner—Kyle L. Howell
Assistant Examiner—T. J. Wallen
Attorney, Agent, or Firm—Linda G. Bierman; Jordan B. Bierman

[57] ABSTRACT

In an adhesive bandage comprising a support and an adhesive layer on the front thereof, the improvement which comprises a thermosetting, water-impermeable lacquer layer on the back of the support, the lacquer layer being less elastic in at least one direction than the support, whereby movement of the body, once the strip has been applied to the skin, will cause cracking of the lacquer layer.

9 Claims, No Drawings

WATER RESISTANT ADHESIVE STRIP

The present invention is directed to a water-resistant adhesive strip especially intended for medical purposes. It consists of a support comprising a non-woven web which is provided on the front side with an adhesive material and carries a water-impermeable coating of a particular kind on its back.

There are a number of special requirements for a high grade adhesive bandage for ordinary human use. Not only must there be good adhesivity to the skin and good tolerance of the skin for the adhesive, but also permeability to water vapor and air. Moreover, comfortable wearing properties, easy and complete detachability, and stability toward mechanical stress are all highly desirable. In particular, the bandage should exhibit good water resistance and protect the wound from the external action of moisture without inhibiting the "breathing" of the skin.

Prior art bandages have been made of cotton or rayon staple fabric with an adhesive material having a rubber resin base. Such products are deficient in a number of the aforementioned requirements, especially with respect to good water-resistance.

A first step toward achieving good water stability, in conjunction with advantageous wearing properties, resulted from the use of thermoplastic soft foils, such as polyvinyl chloride or polyethylene, as substrates. However, since these materials are substantially vapor-impermeable, they must be perforated mechanically in order to provide sufficient vapor-permeability to allow adequate adhesivity to the skin. Because of the size of the holes produced by such mechanical perforation, the protective effect of the bandage against moisture is substantially and undesirably reduced. Microporous foils do not present this disadvantage but, since for technical reasons they have a thickness of 1 to 2 mm, they are relatively thick and bulky.

Bandages are provided with a non-woven web substrate and a micro-porous coating of a polyacrylate-based adhesive material applied thereon by a special method. Such bandages have good adhesivity to the skin and are readily detached leaving no residue. In addition, such adhesives are tolerated very well by the skin. Moreover, due to the fact that there are no double bonds in the adhesive, they will resist storage much better than rubber-based adhesives.

The support materials used impart excellent wearing properties to the bandages; that is, they are soft, pliable, and permeable to air and water vapor. A combination of these two elements makes it possible to fulfill most of the requirements for an ideal bandage, with the exception of stability under mechanical load and resistance to moisture. These last two unsolved problems have hindered the expansion of the use of bandages of this kind.

It is therefore among the objects of the present invention to improve the stability of non-woven web bandages to both mechanical loading and the action of external water, while preserving all of the other desirable properties. In order to achieve this end, it was necessary to find a coating system whereby the porous web substrate is provided with a firm and water-impermeable layer so that bandages made therefrom are sufficiently stable mechanically and are water resistant. At the same time, the substrate must be microporous to permit "breathing" of the skin.

The present invention has been successful in fulfilling these two apparently contradictory requirements without the necessity of a compromise. It has required a particular selection of a suitable web support in conjunction with a special coating system.

The water-resistant adhesive strip according to the present invention comprises a support and an adhesive layer on the front thereof. The support is a thin, porous fiber web which is elastic in at least one direction and has a pore size of 0.5 to 2.0 mm. The back of the support is coated with a thermosetting, water-impermeable lacquer layer about 5 to about 10 microns thick. The lacquer layer is joined to the web by a porous, elastic intermediate layer which is about 1 to 3 microns thick. It is a feature of the present invention that the lacquer layer is less elastic (in at least one direction) than the support.

Thus, when the bandage has been applied to the skin, the thermosetting lacquer layer will crack and produce fine hairline fissures resulting from the natural movements of the skin and the stresses caused thereby. The intermediate layer transmits these stresses from the support to the outer lacquer layer. As a result, the bandage is provided with the air permeability necessary to permit the skin to "breathe" while impermeability to external water is preserved.

It has been found that the support must have a pore size of 0.5 to 2 mm in diameter in order to insure the formation of the hairline cracks in the lacquer layer. As the web pore size is reduced, a thinner coating is necessary in order to achieve a porosity in the lacquer layer by the forces resulting from the normal movement of the skin. However, a coating thinner than about five microns would no longer provide the necessary water resistance. On the other hand, pores larger than about 2 mm would not produce a usable product.

In a preferred form of the invention, the web support comprises polyester fibers which have been strengthened without binder by the "spunlaced" process which uses fine water jets. In this process, fiber webs produced by the dry or wet method can be used. Strengthening occurs in that the fiber web is continuously passed under several sets of nozzles at a distance of a few centimeters. During this passage, it is supported, for example, on a wire screen or perforated plate which imparts its respective hole pattern on the finished web. Water flows out of the nozzle openings under high pressure, which is frequently between 14 and 70 kp/cm$^2$ at the openings. The water jets, impinging on the web, exert an action similar to that found in needle felting; that is, individual fibers are pulled downward by the liquid jet, and are tangled and interlaced with one another due to the turbulent water flow within the web.

Particularly suitable as the thermosetting lacquer layer are the highly crosslinked urea-formaldehyde resins which have been etherified with butanol. Also particularly suitable are lacquers based upon melamine resins which may be combined with alkyd resins. These materials exhibit particularly good resistance to aging and, hence, are especially stable. The thickness of the thermosetting lacquer layer should be only about 5 to 10 microns, preferably about 6 microns. The lacquer in this thickness provides the desired water impermeability and, at the same time, will break open in fine hairline cracks as a result of the normal movement of the skin. This is accomplished without impairing the elastic pliable properties of the web.

The elastic intermediate layer, which connects the thermosetting lacquer layer with the web, can be formed of those polymer compositions which will react completely to a final, elastic, non-tacky state after having been spread on the support material. At the same time, they must still be able, in this condition, to form a good bond both with the web and the lacquer layer. In this way, the desired resistant laminate product is obtained. Preferably, polyurethane-forming mixtures are desirable. These will react to form the end product in situ.

The thickness of the intermediate layer should be only a few microns; that is, about 1 to about 3 microns, preferably about 1 to about 2 microns. If these parameters are observed, the porosity required for a suitable bandage will be obtained. Such a thin layer will automatically tear open to form fine pores in the same manner as the lacquer layer.

On the front or skin side of the support, there is provided a micro porous layer which is applied in known manner, preferably in accordance with German Pat. No. 1,569,901. This layer is also torn open due to the porous structure of the web to form a plurality of larger, perceptible pores.

The desirable adhesive compounds are those which do not irritate the skin and which the skin can tolerate readily. These have proven to be, in particular, those which are based on polyacrylate acid esters or acrylic acid ester copolymers.

The adhesive strip of the present invention, which may be dyed skin color, can be used as an adhesive surgical tape and as a combination adhesive and support material for surgical dressings. In this case, it is preferred that the web be transversely elastic, so that the bandage produced therefrom is elastically stretchable in the same direction. Thus, it can adapt itself particularly well to the movements of the skin without becoming detached.

The dressing may consist of a woven, knit, nonwoven, or foam material. Particularly suitable are those materials which, under the influence of secretions from the wound, do not stick to the surface thereof and which are very absorbant and air permeable. Also preferred are woven or knit fabrics with alternately shrinking and non-shrinking or highly twisted threads, which lift off the wound surface under the action of moisture.

The following example will illustrate the invention.

EXAMPLE

A solvent-containing urea-formaldehyde lacquer is applied in a thickness of 6 g/m² dry weight on a polyester foil 25 microns thick using a roll applicator. The lacquer comprises 77.6 parts by weight of a urea-formaldehyde resin etherified with butanol and having an acid number of 15-20, and 21.4 parts by weight of a urea-formaldehyde resin etherified with butanol and having an acid number of 6-10, and 1.0 parts by weight of p-toluene sulfonic acid, all dissolved in a mixture of butanol, isopropanol and acetone. After removal of the solvents, the lacquer layer is crosslinked in a tunnel dryer at temperatures between 120° and 150° C.

In the next step, 1 to 2 g/m² of a solvent-containing two-component polyurethane adhesive are applied on the fully crosslinked lacquer layer, again using a roll applicator. The layer is so thin that, when dried, a coherent film cannot form. As a base component is used a prepolymer with terminal isocyanate groups and, as the crosslinking component, a hydroxyl-containing compound (a commercial hardener consisting basically of bivalent alcohols).

On the still tacky backing composition, a particularly skin-gentle polyester web produced by the "spunlaced" process, which has a hole pattern similar to a perforation, is applied, and the laminate product is heated in a tunnel dryer to about 80°-100° C. As a result, anchoring on the web support is effected. After this step, the polyester foil used as the auxiliary support is removed and one obtains the waterproofed web support, from which the bandage is made by suitable coating with an adhesive material. This coating process is carried out according to German Pat. No. 1,569,901.

There is provided a viscoelastic adhesive composition obtained by copolymerization of 490 parts by weight of 2-ethyl-hexyl acrylate, 490 parts by weight of n-butyl acrylate, and 20 parts by weight of glycidyl methacrylate, from a solution in an acetone-gasoline mixture. The composition is applied to a paper support provided with a cured silicon coating in a quantity such that, after drying, a layer thickness of about 30 g/m² is obtained. By rapid evaporation of the solvent, the drying process is carried out so that there forms, in the adhesive composition, a plurality of bubbles having a diameter of about 5-15 microns. Onto the dried adhesive composition, the waterproofed web is then laminated with application of pressure, the bubbles being destroyed, and porous to microporous pores are formed in the adhesive layer. The water-resistant coating on the other side of the web is not impaired thereby because, due to the nature of the invention, the coating reacts only to tension and not to compressive stress.

Subsequently, the laminate is heated in a tunnel dryer at about 130° C. to crosslink the self-adhesive material and to anchor it to the web by the reaction occurring between the glycidyl methacrylate groups of the adhesive and the polyester groups thereof.

In processing to form a bandage, the separating paper used as the intermediate support is removed, the absorbant dressing is applied, and the finished strip again covered with siliconized paper or with an adhesive-repellent foil and packaged for sale. If desired, the bandages can, after packing, be sterilized by gamma radiation.

The bandage, when applied to the skin, exhibits excellent air permeability. As a result, it "breathes" very well and is comfortable to wear. This results from the particular coating process of the adhesive composition coupled with the formation of hairline cracks in the waterproof coating of the porous web brought about by stresses generated by movements of the skin. If desired, these cracks can be enlarged by exerting a light tensile stress when applying the bandage.

In order to demonstrate the existence of the cracks, the waterproofed web, with and without the adhesive, was stretched to different degrees and the air permeability (using the Gurley densometer), as well as the vapor permeability, was measured. The results are set forth in the following table and they confirm the effect of elastic elongation of the bandage on these characteristics.

TABLE

| Elongation in % | Air permeability: cc/cm²/sec | | Water vapor permeability: g H₂O/m²/24h | |
|---|---|---|---|---|
| | Web with water-resistant coating | Web with water-resistant coating and self adhesive layer | Web with water resistant coating | Web with water resistant coating and self-adhesive coating |
| 0 | 0 | 0 | 505 | 424 |
| 10 | 3.1 | 0.55 | 750 | 490 |
| 20 | 12.9 | 3.1 | 978 | 552 |
| 40 | >30 | 7.7 | 1215 | 792 |

While only a limited number of specific embodiments of this invention have been expressly disclosed, it is, nonetheless, to be broadly construed and not be limited except by the character of the claims appended hereto.

What we claim is:

1. In a water-resistant adhesive strip comprising a support having a back and front, and an adhesive layer on said front, the improvement which comprises said support being a porous, thin fiber web, elastic in at least one direction, and having a pore size of 0.5 to 2.0 mm, a thermosetting, water-impermeable lacquer layer about 5 to about 10 microns thick on said back, said lacquer layer is joined to said web by a porous, elastic intermediate layer, said lacquer layer being less elastic than said support in at least one direction, whereby cracking of said lacquer layer occurs under stretching of said support.

2. A strip according to claim 1 wherein said support is a binder-free polyester.

3. A strip according to claim 1 wherein said lacquer layer consists of at least one highly crosslinked urea-formaldehyde resin etherified with butanol.

4. A strip according to claim 1 wherein said intermediate layer is a polyurethane.

5. A strip according to claim 1 wherein said adhesive layer comprises at least one polyacrylic acid ester or at least one acrylic acid ester copolymer, said layer being porous.

6. A strip according to claim 1 which is stretchable in its transverse direction.

7. A strip according to claim 1 having a surgical dressing on part of said front, there being a part of said adhesive layer exposed and adopted to contact the skin of the user.

8. A strip according to claim 7 wherein said part comprises a zone on at least two opposite sides of said dressing.

9. A strip according to claim 1 wherein said lacquer layer is joined to said web by a porous, elastic intermediate layer about 1 to 3 microns in thickness.

* * * * *